(12) United States Patent
Zhou (10) Patent No.: US 6,974,533 B2
(45) Date of Patent: Dec. 13, 2005

(54) PLATINUM ELECTRODE AND METHOD FOR MANUFACTURING THE SAME

(75) Inventor: Dao Min Zhou, Saugus, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 95 days.

(21) Appl. No.: 10/226,976

(22) Filed: Aug. 23, 2002

(65) Prior Publication Data

US 2003/0192784 A1 Oct. 16, 2003

Related U.S. Application Data

(60) Provisional application No. 60/372,062, filed on Apr. 11, 2002.

(51) Int. Cl.[7] ............................ C25D 3/50; B32B 15/01
(52) U.S. Cl. ........................ 205/264; 205/83; 205/84; 428/670; 428/687; 428/935
(58) Field of Search ............................ 205/264, 83, 84; 428/670, 687, 935

(56) References Cited

U.S. PATENT DOCUMENTS

| | | |
|---|---|---|
| 4,240,878 A | 12/1980 | Carter |
| 5,109,844 A | 5/1992 | De Juan, Jr., et al. |
| 5,571,158 A | 11/1996 | Bolz, et al. |
| 5,609,611 A | 3/1997 | Bolz, et al. |
| 5,632,770 A | 5/1997 | Schaldach |
| 5,822,177 A | 10/1998 | Popp, et al. |
| 5,871,511 A | 2/1999 | Bolz, et al. |
| 5,935,155 A | 8/1999 | Humayun, et al. |
| 5,964,794 A | 10/1999 | Bolz, et al. |
| 6,219,581 B1 | 4/2001 | Schaldach, et al. |
| 6,230,061 B1 | 5/2001 | Hartung |
| 6,292,703 B1 | 9/2001 | Meier, et al. |
| 6,522,924 B1 | 2/2003 | Meier |

OTHER PUBLICATIONS

"Platinized Platium Electrodes",A.M. Feltham and M. Spiro, Department of Chemistry, Imperial College of Science and Technology, London S.W.7, England; Chemical Reviews, 1971, vol. 71, No. 2; pp. 178-193, no month.

"Fractal Coated Leads: Advanced Surface Technology of Genuine Sensing and Pacing", M. Schaldach, Department of Biomedical Engineering, Erlangen-Nuremberg, Germany Progress in Biomedical Research, Jun. 2000; pp. 259-272.

*Primary Examiner*—Robert R. Koehler
(74) *Attorney, Agent, or Firm*—Scott B. Dunbar; Joseph P. Hamilton (57) ABSTRACT

An improved electrode and method for manufacturing the improved electrode wherein the electrode having a fractal surface coating of platinum [which the present inventor refers to as "platinum gray"] with a increase in surface area of at least 5 times when compared to shiny platinum of the same geometry and also having improved resistance to physical stress when compared to platinum black having the same surface area. The process of electroplating the surface coating of platinum gray comprising plating at a moderate rate, i.e., at a rate that is faster than the rate necessary to produce shiny platinum and that is less than the rate necessary to produce platinum black.

38 Claims, 7 Drawing Sheets

PLATINUM ELECTRODE AND METHOD FOR MANUFACTURING THE SAME

CROSS REFERENCE TO RELATED APPLICATIONS

This application is related to U.S. patent application "Implantable Retinal Electrode Array Configuration for Minimal Retinal Damage and Method of Reducing Retinal Stress" Ser. No. 09/783,236 filed Feb. 13, 2001, which is incorporated herein by reference.

This applications claims priority to U.S. application "Improved Platinum Deposition for Electrodes," Ser. No. 60/372,062, filed on Apr. 11, 2002, the disclosure of which is incorporated herein by reference.

FEDERALLY SPONSORED RESEARCH

This invention was made with government support under grant No. R24EY12893-01, awarded by the National Institutes of Health. The Government has certain rights in the invention.

FIELD OF THE INVENTION

The field of the invention relates to platinum electrodes and electroplating processes for deposition of platinum.

BACKGROUND

Electrodes for stimulating body tissue by electrical stimulation are known in great variety. For the utility of an implantable stimulation or sensing electrode—especially one intended for long-term use in a tissue stimulator with a non-renewable energy source and that, therefore, must require minimal energy—a high electrode capacitance and correspondingly low electrical impedance is of great importance. Furthermore, without sufficiently low impedance, a large voltage may cause polarization of both the electrode and the tissue to which the electrode is attached forming possibly harmful byproducts, degrading the electrode and damaging the tissue.

Because the ability of an electrode to transfer current is proportional to the surface area of the electrode and because small electrodes are necessary to create a precise signal to stimulate a single nerve or small group of nerves, many in the art have attempted to improve the ability of an electrode to transfer charge by increasing the surface area of the electrode without increasing the size of the electrode.

Due to platinum's superior electrical characteristics, biocompatibility and stability, it has often been used as a material for electrodes in corrosive environments such as the human body. While platinum has many desirable qualities for use as an electrode for electrical stimulation of body tissue, because platinum has a smooth surface, its surface area is limited by the geometry of the electrode, and therefore, it is not efficient for transferring electrical charge. The present inventor refers to this platinum with a smooth surface as "shiny platinum".

One approach to increase the surface area of a platinum electrode without increasing the electrode size—and therefore to improve the ability of the electrode to transfer charge—is to electroplate platinum rapidly such that the platinum molecules do not have time to arrange into a smooth, shiny surface. Instead, the rapid electroplating forms what is commonly known as platinum black. Platinum black has a porous and rough surface which is less dense and less reflective than shiny platinum. U.S. Pat. No. 4,240,878 to CARTER describes a method of plating platinum black on tantalum.

Precisely because platinum black is more porous and less dense than shiny platinum, platinum black has weak structural and physical strength and is therefore not suitable for applications where the electrode is subject to even minimal physical stresses. Platinum black also requires additives such as lead to promote rapid plating. Lead, however, is a neurotoxin and cannot be used in biological systems. Finally, due to platinum black's weak structure, the plating thickness is quite limited. Thick layers of platinum black simply fall apart.

For the foregoing reasons there is a need for an improved platinum electrode and process for electroplating the electrode such that the electrode has increased surface area for a given geometry and at the same time is structurally strong enough to be used in applications where the electrode is subject to physical stresses.

SUMMARY OF THE INVENTION

The present invention is directed in part to an electrode having the increased surface area for greater ability to transfer charge and also having sufficient physical and structural strength to withstand physical stress encountered in its intended use.

This and other aspects of the present invention which may become obvious to those skilled in the art through the following description of the invention are achieved by an improved electrode and method for manufacturing the improved electrode wherein the electrode having a fractal surface coating of platinum [which the present inventor refers to as "platinum gray"] with a increase in surface area of at least 5 times when compared to shiny platinum of the same geometry and also having improved resistance to physical stress when compared to platinum black. The gray color of the invention is not considered a feature of the invention. It is a means of describing the invention. The electrodes of the preferred embodiment are too small to display a color without significant magnification. The process of electroplating the surface coating of platinum gray comprising plating at a moderate rate, i.e., at a rate that is faster than the rate necessary to produce shiny platinum and that is less than the rate necessary to produce platinum black.

DETAILED DESCRIPTION OF THE PREFERRED EMBODIMENTS

Figure 1:
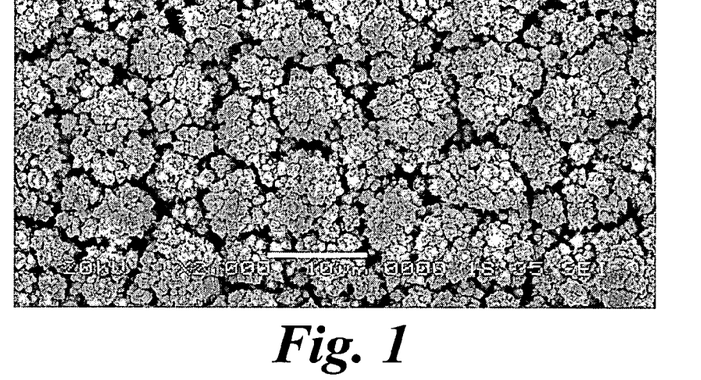
FIG. 1 shows a platinum gray surface magnified 2000 times.
Figure 2:
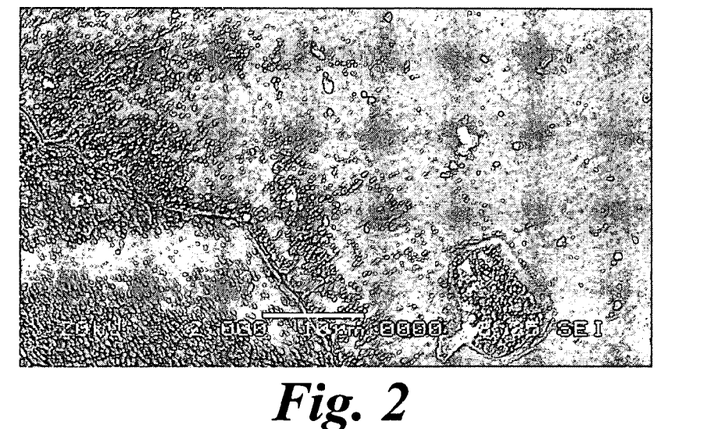
FIG. 2 shows a shiny platinum surface magnified 2000 times.
Figure 3:
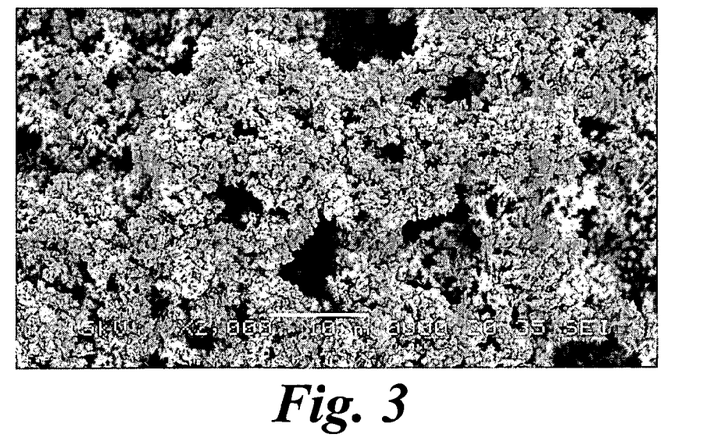
FIG. 3 shows a platinum black surface magnified 2000 times.

Referring to FIG. 1, an illustrative example of a platinum gray surface coating for an electrode according to the present invention is shown having a fractal surface with a surface area increase of greater than 5 times the surface area for a shiny platinum surface of the same geometry, but less than 200 times the surface area of shiny platinum, as is typical of platinum black, shown in FIG. 2, and an increase in strength over a platinum black surface, shown in FIG. 3. FIGS. 1, 2, and 3 are images produced on a Scanning Electron Microscope (SEM) at 2000× magnifications taken by a JEOL JSM5910 microscope (Tokyo, Japan). Under this magnification level it is observed that the platinum gray is of a fractal configuration having a cauliflower shape with particle sizes ranging from 0.5 to 15 microns. Each branch of such structure is further covered by smaller and smaller particles of similar shape. The smallest particles on the surface layer may be in the nanometer range. This rough and porous fractal structure increases the electrochemically active surface area of the platinum surface when compared to an electrode with a smooth platinum surface having the same geometric shape. Because Platinum Grey is plated slower than shiny platinum it can be plated thicker without flaking. Platinum Grey may be plated to 10 microns or thicker.

Because no impurities or other additives such as lead, which is a neurotoxin and cannot be used in an implantable electrode, need to be introduced during the plating process to produce platinum gray, the surface can be pure platinum. Alternatively, other materials such as iridium, rhodium, gold, tantalum, titanium or niobium could be introduced during the plating process if so desired but these materials are not necessary to the formation of platinum gray.

Platinum gray can also be distinguished from platinum black and shiny platinum by measuring the color of the material on a spectrodensitometer using the Commission on Illumination l*a*b* CIELAB color scale. l* defines lightness, a* denotes the red/green value and b*, the yellow/blue value. The lightness value (called l* Value) can range from 0 to 100, where white is 100 and black is 0—similar to grayscale. The a* value can range from +60 for red and −60 for green, and the b* value can range from +60 for yellow and −60 for blue. All samples measured have very small a* and b* values (they are colorless or in the so-called neutral gray zone), which suggests that the lightness value can be used as grayscale for Platinum coatings.

Figure 4:
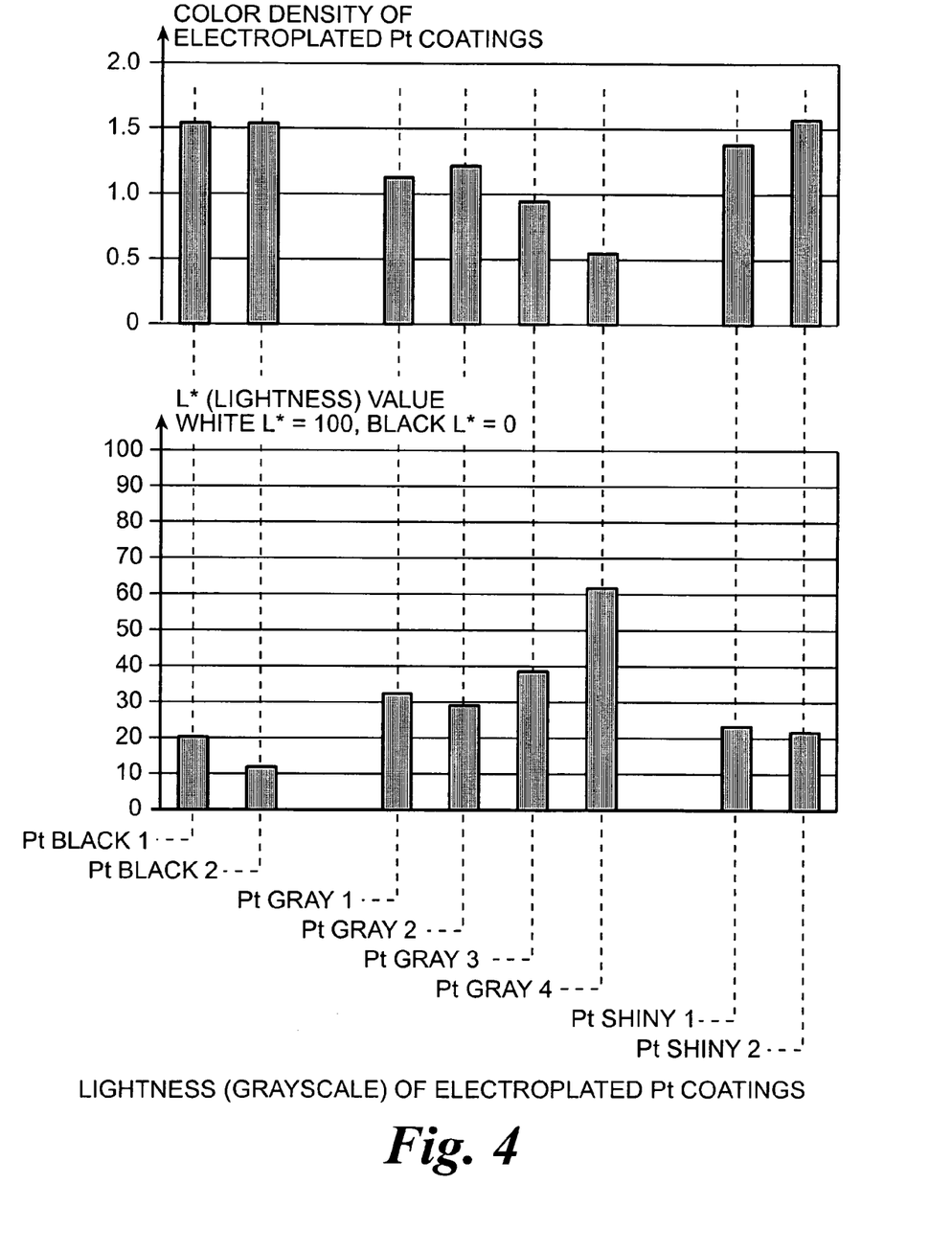
FIG. 4 shows color density (D) values and lightness ($l^*$) values for several representative samples of platinum gray, platinum black and shiny platinum.

Referring to FIG. 4, the l*, a*, and b* values for representative samples of platinum gray, platinum black and shiny platinum are shown as measured on a color reflection spectrodensimeter, X-Rite 520. Platinum gray's l* value ranges from 25 to 90, while platinum black and shiny platinum both have l* values less than 25.

Referring to FIG. 4, color densities have also been measured for representative samples of platinum gray, platinum black and shiny platinum. Platinum gray's color density values range from 0.4 D to 1.3 D, while platinum black and shiny platinum both have color density values greater than 1.3 D.

Platinum gray can also be distinguished from platinum black based on the adhesive and strength properties of the thin film coating of the materials. Adhesion properties of thin film coatings of platinum gray and platinum black on 500 microns in diameter electrodes have been measured on a Micro-Scratch Tester (CSEM Instruments, Switzerland). A controlled micro-scratch is generated by drawing a spherical diamond tip of radius 10 microns across the coating surface under a progressive load from 1 millinewton to 100 millinewtons with a 400 micron scratch length. At a critical load the coating will start to fail. Using this test it is found that platinum gray can have a critical load of over 60 millinewtons while platinum black has a critical load of less than 35 millinewtons.

Referring to FIGS. 5–8, a method to produce platinum gray according to the present invention is described comprising connecting a platinum electrode 2, the anode, and a conductive substrate to be plated 4, the cathode, to a power source 6 with a means of controlling and monitoring 8 either the current or voltage of the power source 6. The anode 2, cathode 4, a reference electrode 10 for use as a reference in controlling the power source and an electroplating solution are placed in a electroplating cell 12 having a means 14 for mixing or agitating the electroplating solution. Power is supplied to the electrodes with constant voltage, constant current, pulsed voltage, scanned voltage or pulsed current to drive the electroplating process. The power source 6 is modified such that the rate of deposition will cause the platinum to deposit as platinum gray, the rate being greater than the deposition rate necessary to form shiny platinum and less than the deposition rate necessary to form platinum black.

Figure 5:
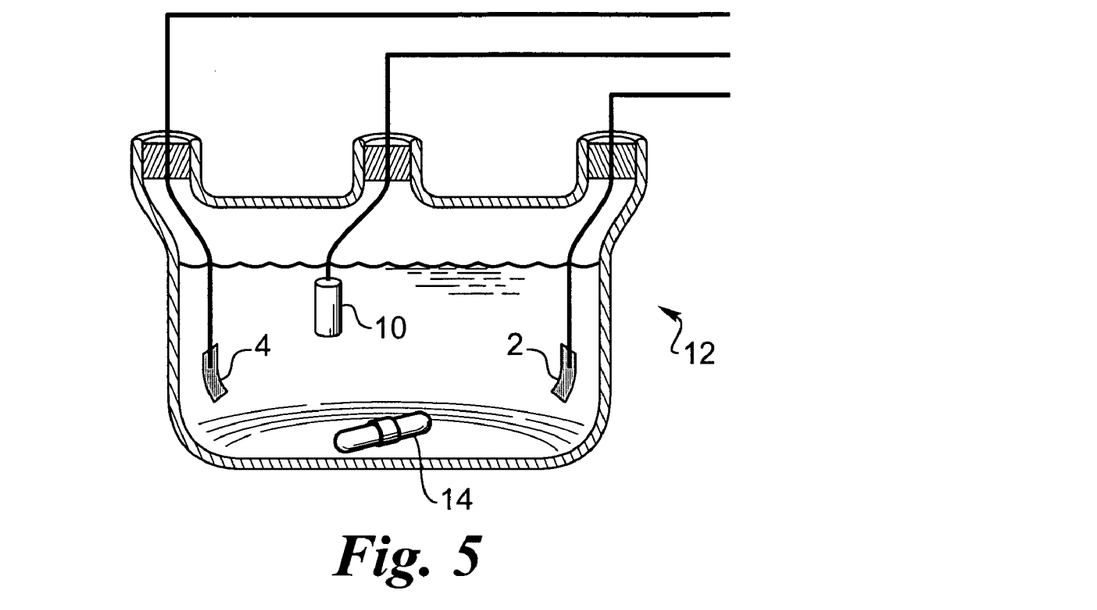
FIG. 5 shows a three-electrode electroplating cell with a magnetic stirrer.
Figure 6:
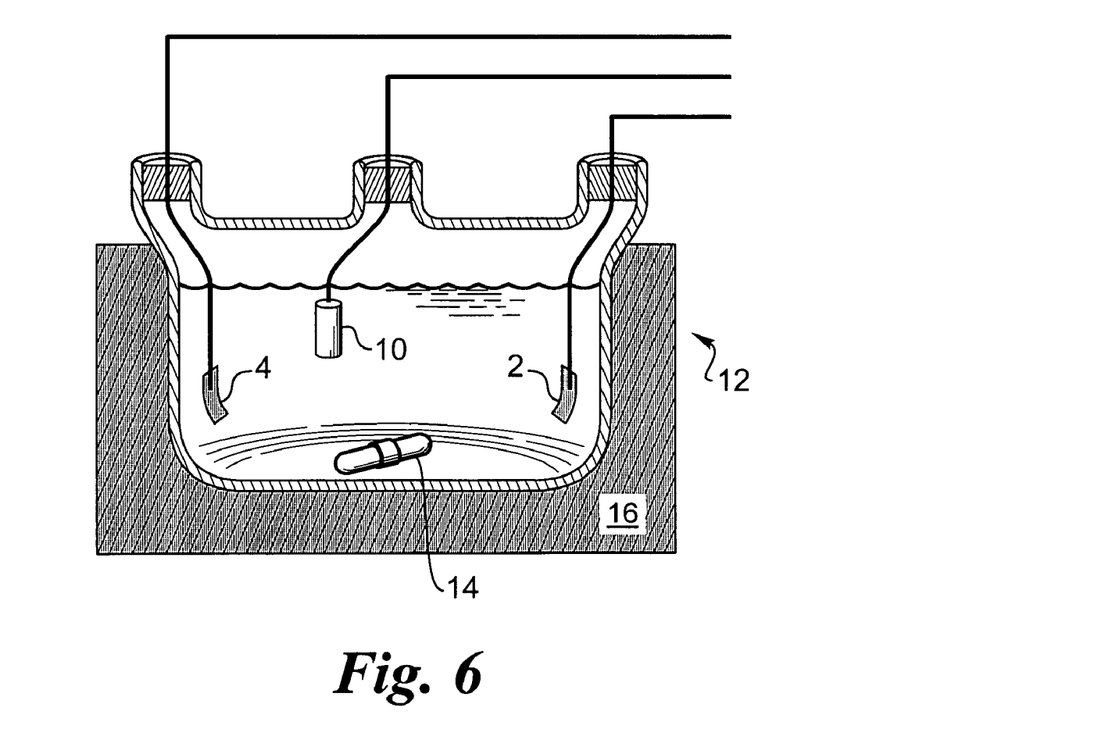
FIG. 6 shows a three-electrode electroplating cell in an ultrasonic tank.
Figure 7:
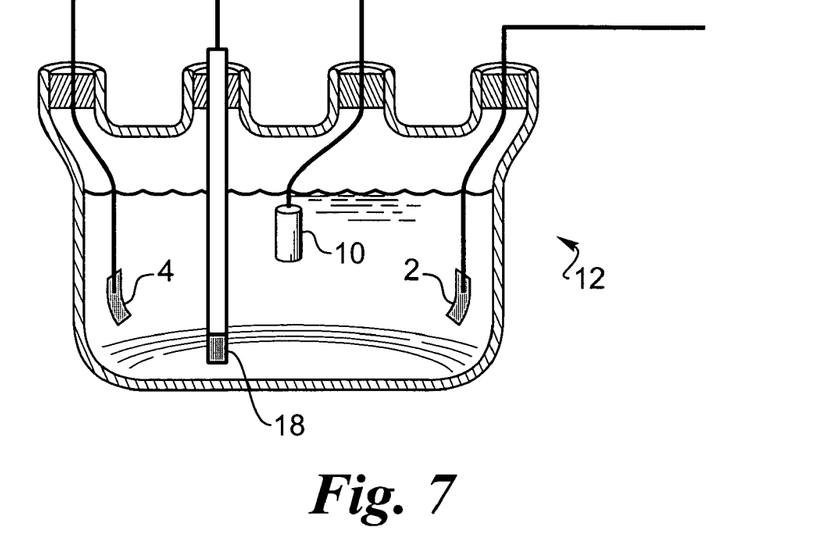
FIG. 7 shows a three-electrode electroplating cell with a gas dispersion tube.
Figure 8:
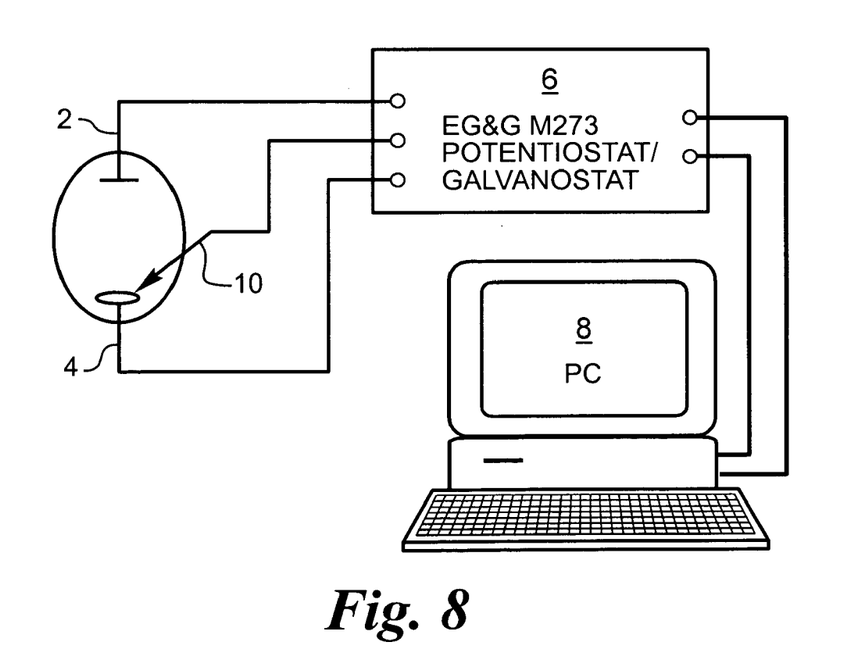
FIG. 8 shows an electroplating system with constant voltage control or constant current control.

Referring to FIGS. 5, 6 and 7, the electroplating cell 12, is preferably a 50 ml to 150 ml four neck glass flask or beaker, the common electrode 2, or anode, is preferably a large surface area platinum wire or platinum sheet, the reference electrode 10 is preferably a Ag/AgCl electrode (silver, silver chloride electrode), the conductive substrate to be plated 4, or cathode, can be any suitable material depending on the application and can be readily chosen by one skilled in the art. Preferable examples of the conductive substrate to be plated 4 include but are not limited to platinum, iridium, rhodium, gold, tantalum, titanium or niobium.

The stirring mechanism is preferably a magnetic stirrer 14 as shown in FIG. 5, an ultrasonic tank 16 (such as the VWR Aquasonic 50 D) as shown in FIG. 6, or gas dispersion 18 with Argon or Nitrogen gas as shown in FIG. 7. The plating solution is preferably 3 to 30 mM (milimole) ammonium hexachloroplatinate in disodium hydrogen phosphate, but may be derived from any chloroplatinic acid or bromoplatinic acid or other electroplating solution. The preferable plating temperature is approximately 24–26 degrees Celsius.

Figure 9:
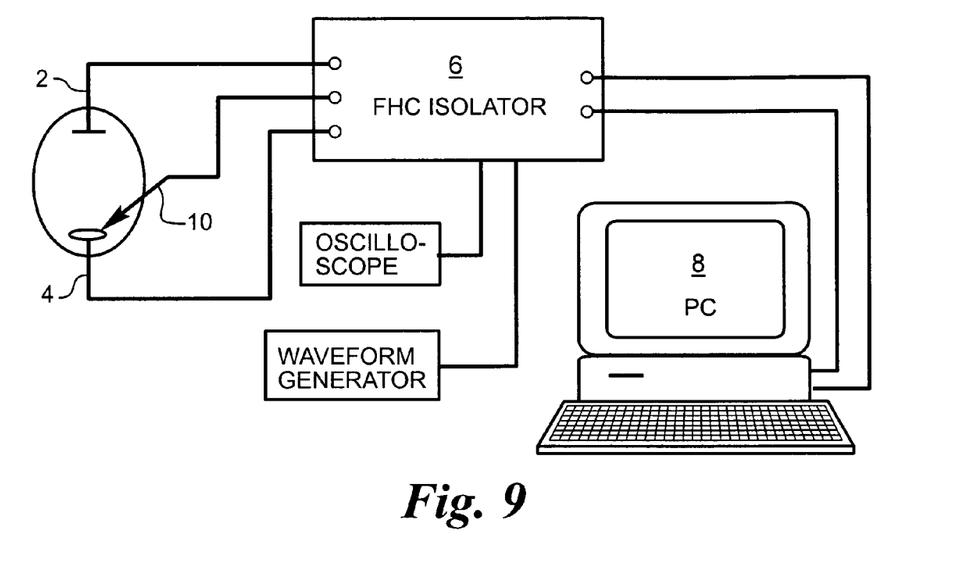
FIG. 9 shows an electroplating system with pulsed current control.
Figure 10:
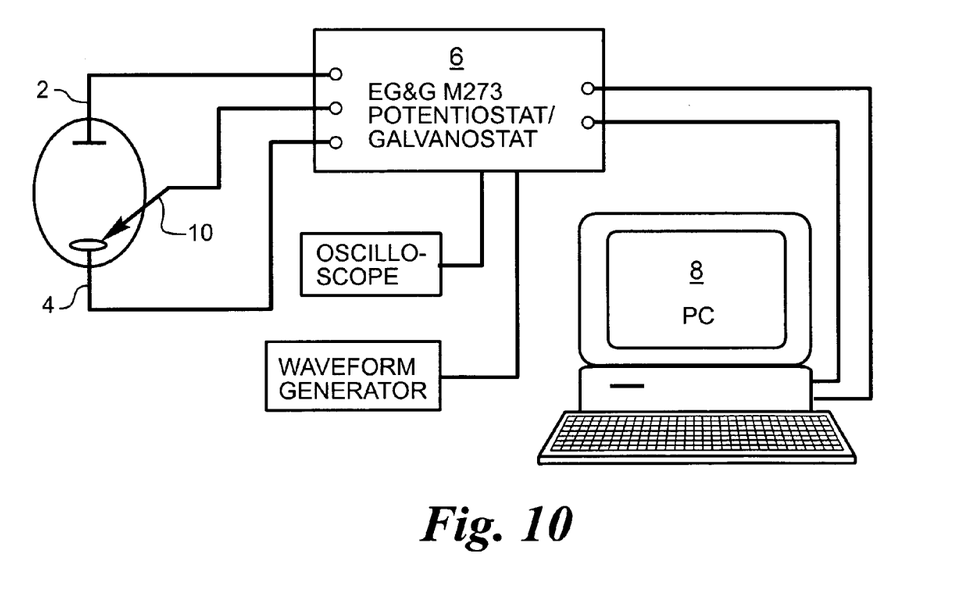
FIG. 10 shows an electroplating system with pulsed voltage control.
Figure 11:
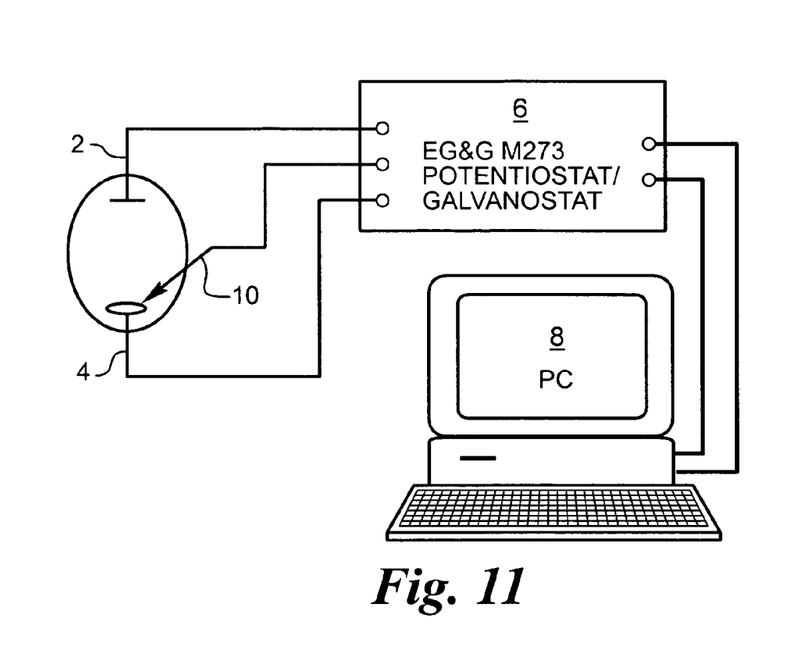
FIG. 11 shows an electroplating system with scanned voltage control.

Electroplating systems with pulsed current and pulsed voltage control are shown in FIGS. 9 and 10 respectively. While constant voltage, constant current, pulsed voltage or pulsed current can be used to control the electroplating process, constant voltage control of the plating process has been found to be most preferable. The most preferable voltage range to produce platinum gray has been found to be −0.45 Volts to −0.85 Volts. Applying voltage in this range with the above solution yields a plating rate in the range of about 1 micron per minute to 0.05 microns per minute, the preferred range for the plating rate of platinum gray. Constant voltage control also allows an array of electrodes in parallel to be plated simultaneously achieving a fairly uniform surface layer thickness for each electrode.

Figure 14:
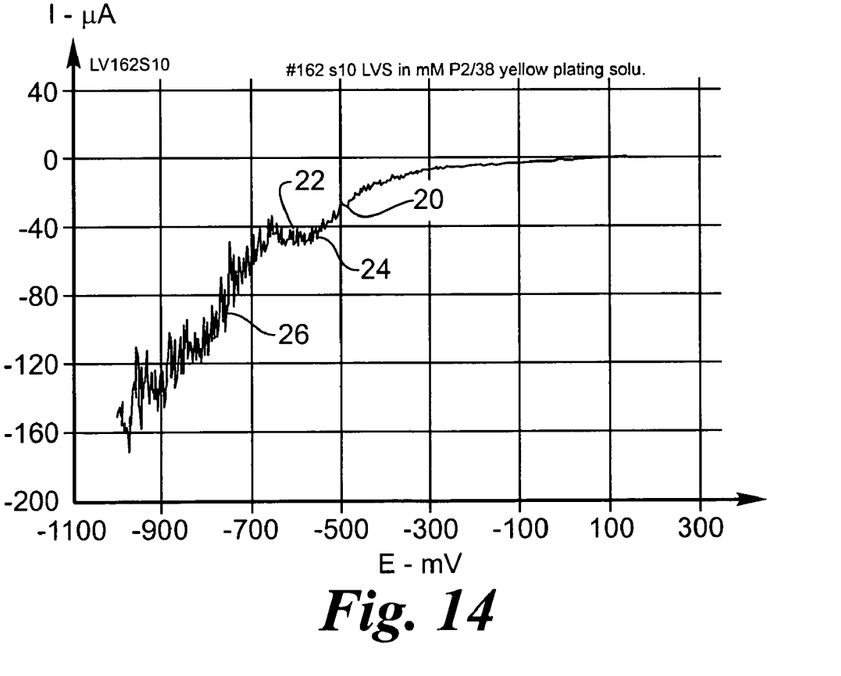
FIG. 14 shows a representative linear voltage sweep of a representative platinum electrode.

The optimal potential ranges for platinum gray plating are solution and condition dependent. Linear voltage sweep can be used to determine the optimal potential ranges for a specific plating system. A representative linear voltage sweep is shown in FIG. 14. During linear voltage sweep, the voltage of an electrode is scanned cathodically until hydrogen gas evolution occurs revealing plating rate control steps of electron transfer 20 and diffusion 22. For a given plating system, it is preferable to adjust the electrode potential such that the platinum reduction reaction has a limiting current under diffusion control or mixed control 24 between diffusion and electron transfer but that does not result in hydrogen evolution 26.

Furthermore, it has been found that because of the physical strength of platinum gray, it is possible to plate surface layers of thickness greater than 30 microns. It is very difficult to plate shiny platinum in layers greater than approximately several microns because the internal stress of the dense platinum layer which will cause the plated layer to peel off and the underlying layers cannot support the above material. The additional thickness of the plate's surface layer allows the electrode to have a much longer usable life.

The following example is illustrative of electroplating platinum on a conductive substrate to form a surface coating of platinum gray according to the present invention.

Figure 12:
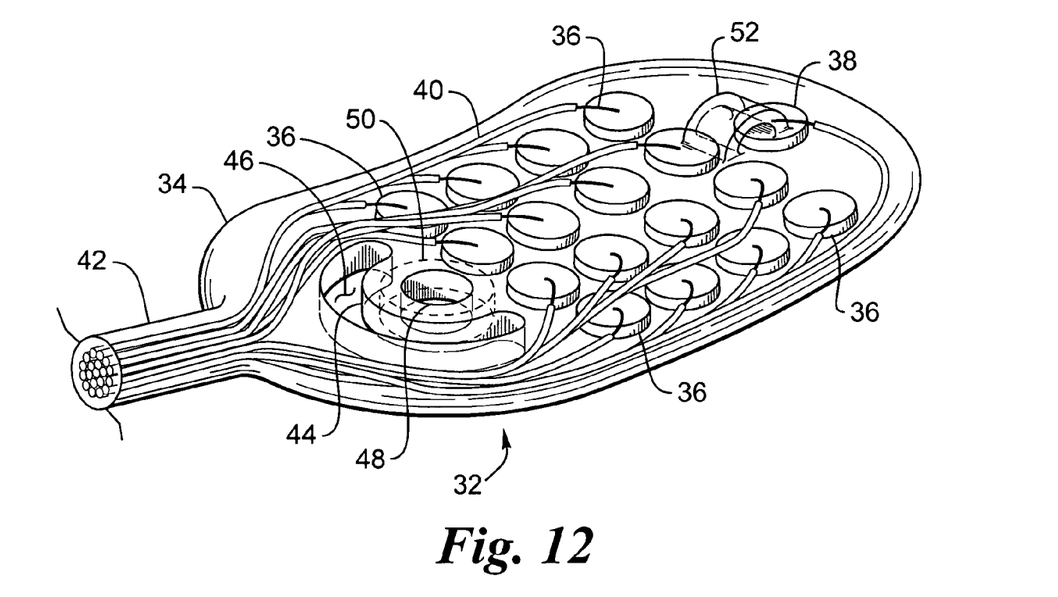
FIG. 12 shows an electrode platinum silicone array having 16 electrodes.

Electrodes with a surface layer of platinum gray are prepared in the following manner using constant voltage plating. An electrode platinum silicone array having 16 electrodes where the diameter of the platinum discs on the array range from 510 to 530 microns, as shown in FIG. 12, is first cleaned electrochemically in sulfuric acid and the starting electrode impedance is measured in phosphate buffered saline solution. Referring to FIG. 5, the electrodes are arranged in the electroplating cell such that the plating electrode 4 is in parallel with the common electrode 42. The reference electrode 10 is positioned next to the electrode array 4. The plating solution is added to the electroplating cell 12 and the stirring mechanism 14 is activated.

A constant voltage is applied on the plating electrode 4 as compared to the reference electrode 10 using an EG&G PAR M273 potentiostat 6. The response current of the plating electrode 4 is recorded by a recording means 8. (The response current is measured by the M273 potentiostat 6.) After a specified time, preferably 1–90 minutes, and most preferably 30 minutes, the voltage is terminated and the electrode array 4 is thoroughly rinsed in deionized water.

The electrochemical impedance of the electrode array with the surface coating of platinum gray is measured in a saline solution. The charge/charge density and average plating current/current density are calculated by integrating the area under the plating current vs. time curve. Scanning Electron Microscope (SEM)/Energy Dispersed Analysis by X-ray (EDAX™) analysis can be performed on selected electrodes. SEM Micrographs of the plated surface can be taken showing its fractal surface. Energy Dispersed Analysis demonstrates that the sample is pure platinum rather than platinum oxide or some other materials.

From this example it is observed that the voltage range is most determinative of the formation of the fractal surface of platinum gray. For this system it observed that the optimal voltage drop across the electrodes to produce platinum gray is approximately −0.55 to −0.65 Volts vs. Ag/AgCl Reference electrode. The optimal platinum concentration for the plating solution is observed to be approximately 8 to 18 mM ammonium hexachloroplatinate in 0.4 M (Mole) disodium hydrogen phosphate.

FIG. 12 provides a perspective view of a retinal electrode array for use with the present invention, generally designated 32, comprising oval-shaped electrode array body 34, a plurality of electrodes 36 made of a conductive material, such as platinum or one of its alloys, but that can be made of any conductive biocompatible material such as iridium, iridium oxide or titanium nitride, and a single reference electrode 38 made of the same material as electrode 36, wherein the electrodes are individually attached to separate conductors 40 made of a conductive material, such as platinum or one of its alloys, but which could be made of any biocompatible conductive material, that is enveloped within an insulating sheath 42, that is preferably silicone, that carries an electrical signal to each of the electrodes 36.

A strain relief internal tab 44, defined by a strain relief slot 46 that passes through the array body 34, contains a mounting aperture 48 for fixation of the electrode array body 34 to the retina of the eye or other neural interface by use of a surgical tack. A reinforcing ring 50 is colored and opaque to facilitate locating the mounting aperture 48 during surgery. A grasping handle 52 is located on the surface of electrode array body 34 to enable its placement by a surgeon using forceps or by placing a surgical tool into the hole formed by grasping handle 52. Grasping handle 52 avoids damage to the electrode body that might be caused by the surgeon grasping the electrode body directly. The electrode array 32 is described in greater detail in U.S. patent application Ser. No. 09/783,236 filed Feb. 13, 2001 and entitled Implantable Retinal Electrode Array Configuration for Minimal Retinal Damage and Method of Reducing Retinal Stress, which is incorporated herein by reference.

Figure 13:
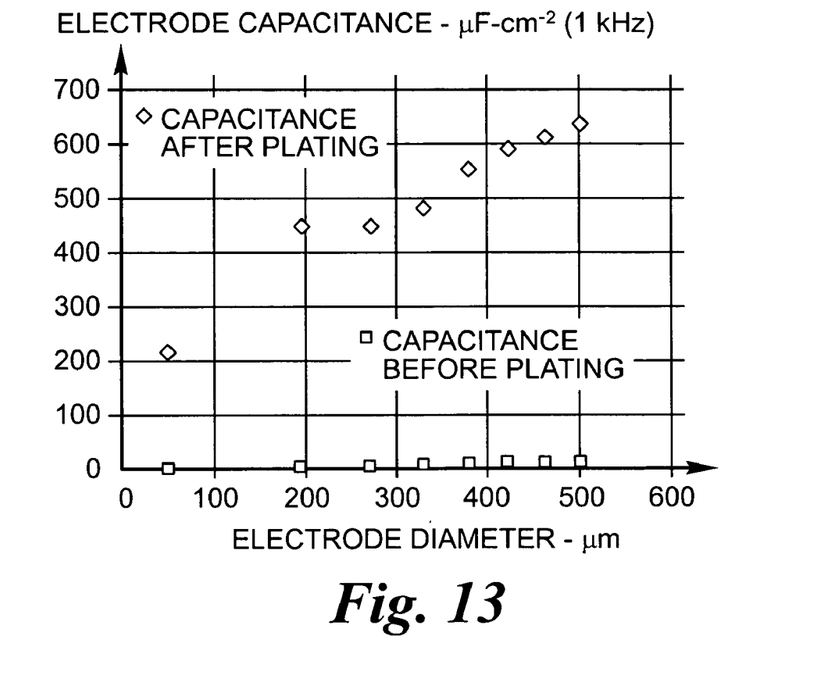
FIG. 13 shows the electrode capacitance for both plated and unplated electrodes of varying diameter.

FIG. 13 shows the increase in electrode capacitance of several electrodes of varying diameter for a polyimide array plated according to the above example at −0.6 V vs. Ag/AgCl Reference electrode for 30 minutes compared with unplated electrodes of the same diameters. Because the electrode capacitance is proportional to its surface area, the surface area increase, calculated from electrode capacitance, is 60 to 100 times that of shiny platinum for this array.

It should be noted that shiny platinum exhibits some roughness and has a surface area increase up to 3 times that of the basic geometric shape. While it is simple to measure a surface area change between two sample using capacitance, it is difficult to compare a sample with the basic geometric shape.

As plating conditions, including but not limited to the plating solution, surface area of the electrodes, pH, platinum concentration and the presence of additives, are changed the optimal controlling voltage and/or other controlling parameters will also change according basic electroplating principles. Platinum gray will still be formed so long as the rate of deposition of the platinum particles is slower than that for the formation of platinum black and faster than that for the formation of shiny platinum.

While the invention is described in terms of a specific embodiment, other embodiments could readily be adapted by one skilled in the art. Accordingly, the scope of the invention is limited only by the following claims.

What is claimed is:

1. An electrode comprising:
   an electrode body; and
   a surface coating of platinum having a fractal configuration.

2. The electrode of claim 1 wherein said surface coating has at least 5 times the surface area of that for the corresponding surface area resulting from the basic geometric shape of the electrode.

3. The electrode of claim 1 wherein said surface coating is biocompatible.

4. The electrode of claim 3 wherein said surface coating does not contain lead.

5. The electrode of claim 3 wherein said surface coating consists essentially of pure platinum.

6. The electrode of claim 2 wherein said surface coating has a surface area of less than 500 times the corresponding surface area resulting from the basic geometric shape.

7. The electrode of claim 2 wherein said surface coating has a surface area of less than 200 times the corresponding surface are resulting from the basic geometric shape.

8. The electrode of claim 7 wherein said surface coating has a thickness of at least 10 microns.

9. The electrode of claim 1 wherein said surface coating has an adhesive strength as measured by critical load greater than 35 millinewtons.

10. The electrode of claim 1 wherein said surface coating appears gray in color.

11. The electrode of claim 1 wherein said surface coating has a lightness (l*) greater than 30 on the CIELAB color scale.

12. The electrode of claim 1 wherein said surface coating has a color density (D) greater than 0.25 D but less than 1.3 D.

13. A method for electroplating a platinum surface coating such that surface has a rough surface coating comprising:
electroplating the surface of a conductive substrate at a rate such that the particles of platinum form on the conductive substrate faster than necessary to form shiny platinum and slower than necessary to form platinum black.

14. The method of claim 13, wherein at least a portion of said rough surface coating has a fractal geometry.

15. The method of claim 13, wherein said step of electroplating is accomplished at a rate of more than 0.05 microns per minute, but less than 1 micron per minute.

16. The method of claim 13, wherein said step of electroplating is accomplished at a rate of greater or equal to 0.01 microns per minute, but less than 10 microns per minute.

17. The method of claim 13 wherein the electroplating process is controlled by electrode voltage.

18. The method of claim 17 wherein said voltage is constant voltage.

19. The method of claim 17 wherein the controlled voltage causes at least a partially diffusion-limited plating reaction.

20. The method of claim 13 wherein the voltage of the electroplating process is less than 0.2 Volts and greater than −1 Volts vs. Ag/AgCl Reference electrode.

21. The method of claim 13 wherein the electroplating solution is at least 3 mM but less than 30 mM ammonium hexachloroplatinate in about 0.4 M disodium hydrogen phosphate.

22. An electrode with a rough surface coating of platinum wherein:
the surface coating is electroplated to the surface of a conductive substrate at a rate such that the particles of platinum form on the conductive substrate faster than necessary to form shiny platinum and slower than necessary to form platinum black.

23. The method of claim 22, wherein at least a portion of said rough surface coating has a fractal geometry.

24. The electrode of claim 22 wherein the electroplating process is controlled by electrode voltage.

25. The electrode of claim 24 wherein the voltage is constant voltage.

26. The method of claim 24 wherein the controlled voltage causes at least a partially diffusion-limited plating reaction.

27. The electrode of claim 24 wherein the voltage of the electroplating process is less than 0.2 Volts and greater than −1 Volts.

28. The electrode of claim 24 wherein the voltage of the electroplating process is less than −0.25 Volts and greater than −1 Volts.

29. The electrode of claim 22 wherein the electroplating solution is at least 3 mM but less than 30 mM ammonium hexachloroplatinate in about 0.4 M disodium hydrogen phosphate.

30. An implantable electrode comprising:
a conductive substrate; and
a rough surface coating having a fractal configuration with between 5 times the surface area and 500 times the surface area of that for the corresponding surface area resulting from the basic geometric shape of the electrode.

31. The implantable electrode of claim 30 wherein the rough surface coating is less than 200 times the surface area of that for the corresponding surface area resulting from the basic geometric shape of the electrode.

32. The implantable electrode of claim 30 wherein the rough surface coating is comprised of platinum.

33. The implantable electrode of claim 31 wherein the rough surface coating is electroplated to the surface of a conductive substrate at a rate such that the particles of platinum form on the conductive substrate faster than necessary to form shiny platinum and slower than necessary to form platinum black.

34. The implantable electrode of claim 33 wherein said rough surface coating has an adhesive strength as measured by a critical load of greater than 35 millinewtons.

35. The implantable electrode of claim 33 wherein said rough surface coating appears gray in color.

36. The electrode of claim 33 wherein said rough surface coating has a lightness (l*) greater than 30 on the CIELAB color scale.

37. The electrode of claim 33 wherein said rough surface coating has a color density (D) greater than 0.25 D but less than 1.3 D.

38. The electrode of claim 33 wherein said rough surface coating having a thickness of at least 10 microns.

* * * * *